(12) United States Patent
Zgorzelski et al.

(10) Patent No.: US 6,855,851 B2
(45) Date of Patent: Feb. 15, 2005

(54) PROCESS FOR PRODUCING ALIPHATIC $C_3$–$C_{10}$-ALCOHOLS FROM HIGH BOILERS

(75) Inventors: Wolfgang Zgorzelski, Oberhausen (DE); Wilhelm Glick, Duisburg (DE)

(73) Assignee: Celanese Chemicals Europe GmbH (DE)

( * ) Notice: Subject to any disclaimer, the term of this patent is extended or adjusted under 35 U.S.C. 154(b) by 0 days.

(21) Appl. No.: 10/701,416

(22) Filed: Oct. 30, 2003

(65) Prior Publication Data

US 2004/0092780 A1 May 13, 2004

(30) Foreign Application Priority Data

Nov. 9, 2002 (DE) .......................................... 102 52 173

(51) Int. Cl.[7] .......................... C07C 29/14; C07C 27/04
(52) U.S. Cl. ........................ 568/880; 568/876; 568/878; 568/881; 568/884; 568/885
(58) Field of Search ................................. 568/876, 878, 568/880, 881, 884, 885

(56) References Cited

U.S. PATENT DOCUMENTS 5,227,544 A  7/1993 Thurman et al.

FOREIGN PATENT DOCUMENTS

EP  0 216 151  4/1987

*Primary Examiner*—Elvis O. Price
(74) *Attorney, Agent, or Firm*—Muserlian, Lucas and Mercanti

(57) ABSTRACT

The present invention relates to a process for producing aliphatic $C_3$–$C_{10}$-alcohols, in particular 2-ethylhexanol, from high boilers by thermal treatment in the presence of an alkali metal compound and subsequent hydrogenation of the volatile products.

8 Claims, No Drawings

US 6,855,851 B2

PROCESS FOR PRODUCING ALIPHATIC $C_3$–$C_{10}$-ALCOHOLS FROM HIGH BOILERS

The present invention relates to a process for producing aliphatic $C_3$–$C_{10}$-alcohols from high boilers by thermal treatment in the presence of alkali metal compounds and subsequent hydrogenation of the volatile products.

Aliphatic $C_3$–$C_{10}$-alcohols, e.g. n-butanol and especially 2-ethylhexanol, have great economic importance. These alcohols are preferably prepared by hydroformylation of olefins with subsequent hydrogenation of the aldehydes formed as intermediates. An economically important example is the hydroformylation of propylene to form n/1-butyraldehyde and subsequent hydrogenation to give n/i-butanol. A further route to aliphatic alcohols is provided by the aldolization of straight-chain aliphatic aldehydes to form the corresponding unsaturated aldehydes and subsequent hydrogenation. An important example of this process is the preparation of 2-ethylhexanol from n-butyraldehyde via the intermediate 2-ethylhexenal. An overview may be found, for example, in Ullmann's Encyclopedia of Industrial Chemistry: "Alcohols, Aliphatic" (Vol. A1), "2-Ethylhexanol" (Vol. 10) and "Butanols" (Vol. A4).

Apart from its use as solvent, n-butanol is used, in particular, in the paint and surface coating sector and for producing carboxylic esters, in particular n-butyl acrylate and di-n-butyl phthalate (DBP). 2-Ethylhexanol is required predominantly as alcohol component for the preparation of di-2-ethylhexyl phthalate (DEHP) and 2-ethylhexyl acrylate.

For these applications, the use of high-purity alcohols is desirable and in many cases, for example the preparation of acrylic esters, absolutely necessary. In the industrial preparation of the alcohols, they are invariably purified by multistage fractional distillation. In such a distillation, the alcohols are subjected to thermal stress, generally at temperatures at the bottom of the column of from 150 to 200° C., for a period of a number of hours. As a result, the distillation of aliphatic $C_3$–$C_{10}$-alcohols results in formation of high boilers which are discharged in the bottoms from the alcohol distillation column. Furthermore, high boilers are formed during the preparation of aliphatic $C_3$–$C_{10}$-alcohols. In particular, the formation of high boilers is observed in the aldolization of n-butyraldehyde to 2-ethylhexenal which precedes the preparation of 2-ethylhexanol and in the subsequent 2-ethylhexenal distillation.

The formation of high boilers in the preparation of aliphatic $C_3$–$C_{10}$-alcohols represents an economic disadvantage because a considerable amount of product of value is lost due to the formation of high boilers and the alcohol yield is thus reduced. In addition, the disposal of the high boilers formed is complicated and expensive. There is therefore a need for a process which reduces the amount of high boilers obtained during the preparation and purification by distillation of aliphatic $C_3$–$C_{10}$-alcohols.

The distillation of alcohols with addition of basic compounds is known from the prior art. In the process known from EP-B1-0 869 936, the addition of from 10 to 1000 ppm of alkali metal hydroxide during the alcohol distillation improves the CO number of the alcohol obtained. The CO number is a measure of the residual aldehyde content. The addition of alkali metal hydroxide enables the formation of aldehydes during the distillation to be reduced and aldehyde present in the alcohol used to be eliminated.

U.S. Pat. No. 2,533,754, too, relates to a process for purifying an aldehyde-containing ethanol with addition of alkali metal hydroxides in an amount of from 0.1 to 3% by weight, based on the alcohol to be purified. In an example, sodium hydroxide is added to an 88.3% strength by weight solution of ethanol in such an amount that the sodium hydroxide content of the solution is 1.46% by weight.

U.S. Pat. No. 2,889,375 discloses a process for the purification by distillation of oxo alcohols containing small amounts of aldehyde compounds as impurities. In the process disclosed, alkaline earth metal compounds, in particular oxides, hydroxides or carbonates, are added to the bottoms from the column in an amount of 1% by weight, based on the feed. However, according to U.S. Pat. No. 2,889,375, the addition of alkali metal compounds such as sodium carbonate or sodium hydroxide during the distillation leads to considerable alcohol losses as a result of the formation of condensation products.

U.S. Pat. No. 3,689,371 discloses a process for the purification by distillation of butanols from the oxo process. The crude alcohol obtained is firstly treated with an aqueous alkali metal hydroxide solution to neutralize or hydrolyze the acids and esters present in the crude alcohol. According to the known process, the alkali metal hydroxides are then removed from the crude alcohol, for example by means of a water scrub, and the crude alcohol which has been freed of alkali metal hydroxide is subsequently passed to further work-up by distillation.

It is known from the prior art that the purification of the alcohols by distillation can be carried out in the presence of small amounts of alkali metal hydroxide in order to increase the purity of the distilled alcohols. However, the prior art does not suggest any treatment of the residues obtained in the preparation and work-up by distillation in order to recover alcohols from the high boilers.

The invention accordingly provides a process for producing aliphatic $C_3C_{10}$-alcohols from high boilers. In this process, the high boilers are brought to a neutralization number of up to 2 mg KOH/g by means of an alkali metal compound and are treated at a temperature of from 165 to 185° C. and a pressure of from 80 to 150 hPa in a distillation column and the overhead product taken off is subsequently hydrogenated.

The high boilers used in the process of the invention are obtained as bottom product in the purification of the alcohols by distillation. These distillation residues are, if appropriate, admixed with further high boilers from the preparation of the alcohols before they are treated by the process of the invention in a separate distillation column. Such high boilers are obtained, for example, in upstream aldolization processes in which aldehydes are firstly condensed to form longer-chain unsaturated aldehydes which are subsequently hydrogenated to give the saturated alcohols. The separate distillation column in which the high boilers are treated by the process of the invention is also referred to as a residue column.

The treatment according to the invention of the high boilers from the preparation and distillation of aliphatic $C_3$–$C_{10}$-alcohols surprisingly leads to dissociation of the high boilers into the corresponding alcohols and aldehydes which are taken off via the top of the column. The overhead product from the residue column, which comprises alcohols and aldehydes, is returned to the hydrogenation stage of the alcohol production process in which the aldehydes present are hydrogenated to form the corresponding alcohols. This makes it possible to reduce the amount of high boilers obtained by about 20% and to increase the alcohol yield compared to the procedure in which a residue column is operated without addition of alkali.

The high boilers discharged at the bottom of the pure distillation column and the high boilers from the alcohol production process which may be added are complex mixtures, for example of ester compounds of aldol condensation products. Although intensified thermal stress in the pure distillation column does lead to a reduction in the residual alcohol content in the high boilers, it also promotes high boiler formation. The residual content of aliphatic $C_3$–$C_{10}$-alcohols naturally depends on the distillation conditions in the residue column and is generally in a range from 3 to 5%, based on the total amount of residue.

To produce valuable aliphatic $C_3$–$C_{10}$-alcohols by deliberate dissociation of high boilers, the high boilers obtained are treated in a residue column at a temperature in the range from 165 to 185° C., preferably from 170 to 180° C., in the presence of an alkali metal compound. The amount of alkali metal compound added depends on the residual acid content of the high boilers and is calculated so that the neutralization number of the high boilers is not below 2 mg KOH/g. The neutralization number is determined in accordance with DIN 51 558-01. The alkali metal compound is preferably added in such an amount that the neutralization number of the high boilers is in a range from 2 to 5 mg KOH/g. At dissociation temperatures below 165° C., satisfactory alcohol and aldehyde formation is no longer observed, even when the amount of alkali metal compound added is increased and the neutralization number is brought to below 2 mg KOH/g. Increasing the dissociation temperature to above 185° C. also does not lead to increased alcohol and aldehyde formation, even when the addition of alkali metal compounds is increased.

In the process of the invention, there is therefore a narrow temperature range within which the temperature in the residue column has to be maintained in order to achieve optimal high boiler dissociation.

The alcohols and aldehydes formed by dissociation of high boilers in the residue column are taken off as overhead product and are returned to the hydrogenation stage of the alcohol production process in which the aldehydes are hydrogenated to the corresponding alcohols.

The hydrogenation is carried out in the gas phase under conventional conditions in the presence of customary hydrogenation catalysts as are known, for example, from EP-B1-0 421 196 or EP-B1-0 335 222. Apart from supported catalysts based on nickel, aluminum oxide and zirconium dioxide, it is also possible to use nickel catalysts as are known, for example, from EP-B1-0 618 006. Catalysts comprising copper oxide, e.g. those known from EP-A-0 604 792 or EP-A-0 528 305, are likewise suitable.

A particularly useful hydrogenation catalyst is that described in EP-A0 528 305, which comprises 40–130 parts by weight of zinc oxide, 2–50 parts by weight of aluminum oxide and, if desired, 0.5–8 parts by weight of manganese, molybdenum, vanadium, zirconium and/or alkaline earth metal oxide per 100 parts by weight of copper oxide and has a total BET surface area of 80–175 $m^2$/g of catalyst in the unreduced state, where 75–95% of the total BET surface area is made up by pores having a radius $r_p$ of <15 nm.

The hydrogenation temperature is generally 50–250° C., preferably 80–160° C. The pressure is generally in a range of 0.01–2.5 MPa.

The aliphatic $C_3$–$C_{10}$-alcohols can be linear or branched. The process of the invention can be particularly advantageously used for working up high boilers from the preparation of 2-ethylhexanol. Here, the distillation residues from the purification of 2-ethylhexanol by distillation and the residues obtained in the upstream aldolization of n-butyraldehyde to form 2-ethylhexenal and in the 2-ethylhexenal distillation are combined and treated in the residue column by the process of the invention. The 2-ethylhexanol-, 2-ethylhexenal- and 2-ethylhexanal-containing overhead product is returned to the hydrogenation stage and subsequently passed to the distillation for purifying the 2-ethylhexanol.

Alkali metal compounds used are, for example, hydroxides, carbonates or hydrogencarbonates. Preference is given to sodium hydroxide or potassium hydroxide. The alkali metal hydroxides are added as aqueous solutions, usually solutions having an alkali metal hydroxide content of from 18 to 25% by weight, based on the aqueous solution. However, addition of the alkali metal compounds in solid form is not ruled out.

The alkali metal compound is added to the feed to the residue column and then collects in the liquid phase of the residue column.

The residue column is a customary distillation column which generally has from 20 to 40 plates, preferably from 25 to 35 plates. The residue column can be operated batchwise or continuously.

The process of the invention makes it possible to recover aliphatic $C_3$–$C_{10}$-alcohols and -aldehydes from the high boilers and convert these into alcohols in a subsequent hydrogenation process. Viewed over the entire alcohol production process, the alcohol yield is increased and the total amount of high boilers obtained is reduced.

EXAMPLE

A

The combined high boilers from the preparation of 2-ethylhexanol were brought to a neutralization number of 3 mg KOH/g by addition of an aqueous potassium hydroxide solution (20% strength) and treated at a temperature of 175° C. and a pressure of 90 hPa in a residue column (30 plates). 750 kg/h of high boilers were discharged at the bottom of the residue column, while the overhead product was recirculated to the hydrogenation stage.

B

The residue column was operated as described under A, except that the addition of potassium hydroxide was omitted. 930 kg/h of high boilers were obtained at the bottom of the residue column and were discharged.

The addition according to the invention of alkali metal compounds enables the amount of high boilers obtained to be reduced by about 20% in the process for producing 2-ethylhexanol.

What is claimed is:

1. A process for producing aliphatic alcohols of 3 to 10 carbon atoms from high boilers, comprising adjusting the high boilers to a neutralization number of not below 2 mg of KOH/g by addition of an alkali metal compound and treating the resulting mixture at a temperature of 165 to 185° C. and a pressure of 80 to 150 hPa in a distillation column and overhead product taken off is subsequently hydrogenated.

2. The process of claim 1, wherein the neutralization number is brought to a value in the range from 2 to 5 mg of KOH/g by addition of an alkali metal compound.

3. The process of claim 1 wherein the temperature is 170 to 180° C.

4. The process of claim 1 wherein an aqueous solution of the alkali metal compound is used.

5. The process of claim 1 wherein the alkali metal compound is an alkali metal hydroxide.

6. The process of claim 5, wherein the alkali metal hydroxide is sodium hydroxide or potassium hydroxide.

7. The process of claim 1 wherein the aliphatic alcohol is 2-ethylhexanol.

8. The process of claim 1 wherein the alkali metal compound is added to the feed to the distillation column.

* * * * *